(12) United States Patent
Roh

(10) Patent No.: US 10,980,445 B2
(45) Date of Patent: Apr. 20, 2021

(54) SHOE-TYPE DEVICE AND CONTROL METHOD THEREOF

(71) Applicant: Samsung Electronics Co., Ltd., Suwon-si (KR)

(72) Inventor: Changhyun Roh, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 5 days.

(21) Appl. No.: 16/415,220

(22) Filed: May 17, 2019

(65) Prior Publication Data

US 2020/0187830 A1 Jun. 18, 2020

(30) Foreign Application Priority Data

Dec. 12, 2018 (KR) .................. 10-2018-0159807

(51) Int. Cl.
| | | |
|---|---|---|
| *A61B 5/00* | (2006.01) | |
| *A61B 5/11* | (2006.01) | |
| *A43B 13/00* | (2006.01) | |
| *A43B 3/00* | (2006.01) | |

(52) U.S. Cl.
CPC .......... *A61B 5/1116* (2013.01); *A43B 3/0005* (2013.01); *A61B 5/0051* (2013.01); *A61B 5/6807* (2013.01)

(58) Field of Classification Search
CPC ........... A61B 5/00; A61B 5/11; A61B 5/1116; A43B 3/00; A43B 3/0005
See application file for complete search history.

(56) References Cited

U.S. PATENT DOCUMENTS

| | | |
|---|---|---|
| 4,745,930 A | 5/1988 | Confer |
| 6,978,684 B2 | 12/2005 | Nurse |
| 8,308,665 B2 | 11/2012 | Harry et al. |
| 8,350,671 B2 | 1/2013 | Kim |
| 9,135,792 B2 | 9/2015 | Han et al. |
| 10,595,749 B1 * | 3/2020 | Javitt .................. A61F 5/14 |
| 2007/0159507 A1 | 7/2007 | Urano |
| 2009/0200880 A1 * | 8/2009 | Mortimer ............. B06B 1/10 |
| | | 310/81 |
| 2011/0153197 A1 * | 6/2011 | Song .................. A61B 5/1112 |
| | | 701/533 |
| 2011/0271554 A1 | 11/2011 | Jazdanian |

(Continued)

FOREIGN PATENT DOCUMENTS

| | | |
|---|---|---|
| CN | 201256658 Y | 6/2009 |
| CN | 102499859 A | 6/2012 |

(Continued)

OTHER PUBLICATIONS

Non-Final Office Action dated Apr. 22, 2019 in U.S. Appl. No. 15/403,546.

(Continued)

*Primary Examiner* — Mark A Connolly
(74) *Attorney, Agent, or Firm* — Harness, Dickey & Pierce P.L.C.

(57) ABSTRACT

A shoe-type device and a control method of the shoe-type device are disclosed. A control method of a shoe-type device including an actuator and at least one sensor includes estimating a posture of a user wearing the shoe-type device based on sensor data output from the sensor, and controlling the actuator based on the estimated posture of the user.

18 Claims, 12 Drawing Sheets

(56) References Cited

U.S. PATENT DOCUMENTS

| | | |
|---|---|---|
| 2012/0186101 A1 | 7/2012 | Sanchez |
| 2012/0222333 A1 | 9/2012 | Short et al. |
| 2012/0291564 A1 | 11/2012 | Amos et al. |
| 2013/0072835 A1 | 3/2013 | Harry et al. |
| 2013/0213147 A1 | 8/2013 | Rice et al. |
| 2014/0142475 A1 | 5/2014 | Goldfarb et al. |
| 2014/0316309 A1 | 10/2014 | Seo et al. |
| 2015/0321339 A1 | 11/2015 | Asbeck et al. |
| 2016/0012687 A1 | 1/2016 | Obana et al. |
| 2016/0206499 A1* | 7/2016 | Shim .................. A61B 5/1038 |
| 2016/0206503 A1 | 7/2016 | Planke |
| 2016/0324445 A1* | 11/2016 | Kim .................... A61B 5/1038 |
| 2016/0324487 A1 | 11/2016 | Guo et al. |
| 2016/0366266 A1 | 12/2016 | Chung et al. |
| 2017/0112712 A1 | 4/2017 | Chawan et al. |
| 2017/0156659 A1 | 6/2017 | Yang et al. |
| 2017/0156662 A1 | 6/2017 | Goodall et al. |
| 2017/0265594 A1 | 9/2017 | Walker et al. |
| 2018/0020764 A1 | 1/2018 | Walker |
| 2018/0085281 A1 | 3/2018 | Roh |
| 2018/0168283 A1 | 6/2018 | Agati |
| 2018/0168913 A1 | 6/2018 | Sedic |
| 2018/0199674 A1 | 7/2018 | Walker et al. |
| 2018/0200598 A1 | 7/2018 | Guan et al. |
| 2019/0122507 A1 | 4/2019 | Roh |
| 2020/0289028 A1* | 9/2020 | Oumnia .................. H04W 4/80 |

FOREIGN PATENT DOCUMENTS

| | | |
|---|---|---|
| CN | 203105800 U | 8/2013 |
| CN | 106539182 A | 3/2017 |
| DE | 202008008727 U1 | 9/2008 |
| DE | 102014115135 A1 | 4/2015 |
| EP | 1608303 A2 | 12/2005 |
| EP | 3081160 A1 | 10/2016 |
| IN | 37/2007 | 9/2007 |
| JP | 3151948 B2 | 4/2001 |
| JP | 2006204520 A | 8/2006 |
| JP | 2007268012 A | 10/2007 |
| JP | 2007268056 A | 10/2007 |
| JP | 5189911 B2 | 4/2013 |
| JP | 5741375 B2 | 7/2015 |
| KR | 20050122205 A | 12/2005 |
| KR | 2007-0053911 A | 5/2007 |
| KR | 100946186 B1 | 3/2010 |
| KR | 20120057626 A | 6/2012 |
| KR | 101248190 B1 | 3/2013 |
| KR | 10-1302364 | 9/2013 |
| KR | 101350334 B1 | 1/2014 |
| KR | 101492862 B1 | 2/2015 |
| KR | 20160090088 A | 7/2016 |
| KR | 2017-0143341 A | 12/2017 |
| WO | WO-2008/061420 A1 | 5/2008 |
| WO | WO-2009/039555 A1 | 4/2009 |
| WO | WO-2009105918 A1 | 9/2009 |
| WO | WO-2012/112930 A1 | 8/2012 |
| WO | WO-2015/004498 A1 | 1/2015 |
| WO | WO-2016/191115 A1 | 12/2018 |

OTHER PUBLICATIONS

Final Office Action dated Aug. 7, 2019 in U.S. Appl. No. 15/403,546.
Non-Final Office Action dated Sep. 18, 2018 in U.S. Appl. No. 15/894,320.
Notice of Allowance dated Mar. 6, 2019 in U.S. Appl. No. 15/894,320.
Extended European Search Report dated Feb. 5, 2020 for EP Application No. 19188457.6.
U.S. Appl. No. 15/403,546, filed Jan. 11, 2017.
U.S. Appl. No. 15/894,320, filed Feb. 12, 2018.
Extended European Search Report dated Mar. 3, 2020 for corresponding European Application No. 19191372.2.
Non-Final Office Action dated Apr. 8, 2020 in U.S. Appl. No. 15/403,546.
Bing Chen et al., "Design of a Lower Extremity Exoskeleton for Motion Assistance in Paralyzed Individuals", Proceedings of the 2015 IEEE Conference on Robotics and Biomimetics, Zhuhai, China, Dec. 6-9, 2015, pp. 144-149.
Slavko Rogan et al., "Stochastic resonance whole-body vibration training for chair rising performance on untrained elderly—A pilot study", Archives of Gerontology and Geriatrics 55 Mar. 2012, pp. 468-473.
Attila A. Priplata et al., "Vibrating insoles and balance control in elderly people", The Lancet, vol. 362, Oct. 4, 2003, pp. 1123-1124, www.thelancet.com.
Extended European Search Report dated Jan. 9, 2020 for EP Application No. 19188453.3.
Final Office Action dated Jan. 17, 2020 for U.S. Appl. No. 15/403,546.
U.S. Appl. No. 16/433,435, filed Jun. 6, 2019.
U.S. Appl. No. 16/433,408, filed Jun. 6, 2019.
U.S. Appl. No. 16/433,600, filed Jun. 6, 2019.
Extended European Search Report dated Jan. 24, 2020 for European Patent Application No. 19188429.5.

* cited by examiner

FIG. 9

| Motion size<br>Foot pressure | Large | Middle | Small |
|---|---|---|---|
| Large | Heel-landing | | Standing |
| Middle | | | |
| Small | Toe-off / swing | | Sitting |

910

SHOE-TYPE DEVICE AND CONTROL METHOD THEREOF

CROSS-REFERENCE TO RELATED APPLICATION

This application claims under 35 U.S.C. § 119 to Korean Patent Application No. 10-2018-0159807 filed on Dec. 12, 2018, in the Korean Intellectual Property Office, the entire contents of which are incorporated herein by reference in their entirety.

BACKGROUND

1. Field

At least one example embodiment relates to a shoe-type device and/or a control method of the shoe-type device.

2. Description of the Related Art

A user wears shoes in daily life. The shoes are used to protect feet of the user comfortably and safely. Recently, wearable devices provided in a type of shoes including therein sensors and/or actuators have been developed to sense a walking pattern of a user and assist the user in walking more comfortably and stably.

SUMMARY

Some example embodiments relate to a method of controlling a smart shoe, the smart shoe including an actuator and at least one sensor.

In some example embodiments, the method includes estimating a posture of a user wearing the smart shoe based on sensor data output from the sensor to generate an estimated posture; and controlling the actuator based on the estimated posture of the user.

In some example embodiments, the controlling of the actuator includes selectively stopping an operation of the actuator based on the posture of the user.

In some example embodiments, the selectively stopping the operation of the actuator includes stopping the operation of the actuator in response to the estimated posture of the user being a sitting posture.

In some example embodiments, the selectively stopping the operation of the actuator includes maintaining the operation of the actuator in response to the estimated posture of the user not being a sitting posture.

In some example embodiments, the sensor includes a foot pressure sensor configured to measure a foot pressure of the user to generate the sensor data, and the maintaining the operation of the actuator includes determining a maximum vibration intensity of the actuator based on the sensor data.

In some example embodiments, the determining the maximum vibration intensity of the actuator includes increasing the maximum vibration intensity in response to the foot pressure increasing within a range.

In some example embodiments, the determining the maximum vibration intensity of the actuator includes setting a first maximum vibration intensity of the actuator based on a first foot pressure associated with a first foot of the user, and setting a second maximum vibration intensity of the actuator based on a second foot pressure associated with a second foot of the user such that the second maximum vibration intensity is different from the first maximum vibration intensity.

In some example embodiments, the estimating the posture includes determining whether the estimated posture of the user is a sitting posture based on the sensor data.

In some example embodiments, the sensor includes a foot pressure sensor, and wherein the estimating the posture includes estimating the posture of the user based on a foot pressure measured by the foot pressure sensor and a change in foot pressure over time to generate the estimated posture.

In some example embodiments, the method includes the sensor includes a foot pressure sensor and a motion sensor, the foot pressure sensor configured to measure foot pressure to generate foot pressure information and the motion sensor configured to measure motion size to generate motion information, and wherein the estimating the posture includes estimating the posture of the user based on the foot pressure information and the motion information to generate the estimated posture.

In some example embodiments, the estimating of the posture includes determining the estimated posture of the user as a sitting posture, in response to the foot pressure being less than or equal to a first threshold value and the motion size being less than or equal to a second threshold value.

Some example embodiments relate to a non-transitory computer-readable medium storing computer readable instructions that, when executed, cause a computer to perform a method of controlling a smart shoe.

Other example embodiments relate to a smart shoe.

In some example embodiments, the smart shoe includes an actuator; a foot pressure sensor configured to measure a foot pressure to generate foot pressure information; and a processor configured to, estimate a posture of a user wearing the smart shoe based on at least the foot pressure information to generate an estimated posture, and control the actuator by generating a control signal based on the estimated posture of the user.

In some example embodiments, the processor is configured to control the actuator by selectively stopping an operation of the actuator based on the posture of the user.

In some example embodiments, the processor is configured to control the actuator by generating the control signal to stop the operation of the actuator in response to the estimated posture of the user being a sitting posture.

In some example embodiments, the processor is further configured to determine a maximum vibration intensity of the actuator based on the foot pressure measured by the foot pressure sensor, in response to the processor determining to continue the operation the actuator.

In some example embodiments, the smart shoe further includes a motion sensor configured to measure a motion of the smart shoe to generate motion information, wherein the processor is configured to control the actuator based on the foot pressure information and the motion information.

In some example embodiments, the foot pressure sensor is in a sole of the smart shoe, and the motion sensor is in at least one of the sole or an upper of the smart shoe.

In some example embodiments, the actuator is configured to generate a vibration to apply nerve stimulation to a foot of the user.

Other example embodiments also relate to a smart shoe.

In some example embodiments, the smart shoe includes an actuator; a foot pressure sensor configured to measure a foot pressure of a user wearing the smart shoe to generate foot pressure information; and a processor configured to generate a control signal to control a maximum vibration intensity of the actuator based on at least the foot pressure information.

In some example embodiments, the processor is configured to control the actuator by selectively stopping an operation of the actuator based on the foot pressure information.

In some example embodiments, the processor is further configured to increasing the maximum vibration intensity in response to the foot pressure increasing within a range.

In some example embodiments, the processor is configured to control the maximum vibration intensity by, setting a first maximum vibration intensity of the actuator based on a first foot pressure associated with a first foot of the user, and setting a second maximum vibration intensity of the actuator based on a second foot pressure associated with a second foot of the user such that the second maximum vibration intensity is different from the first maximum vibration intensity.

In some example embodiments, the actuator includes a first actuator and a second actuator, the first actuator being in a first area of the smart shoe and the second actuator being in a second area of the smart shoe, and the foot pressure sensor includes a first foot pressure sensor and a second foot pressure sensor, the first foot pressure sensor being in an area adjacent to the first area and the second foot pressure sensor being in an area adjacent to the second area.

In some example embodiments, the processor is further configured to determine a maximum vibration intensity of the first actuator based on the foot pressure measured by the first foot pressure sensor; and determine a maximum vibration intensity of the second actuator based on the foot pressure measured by the second foot pressure sensor.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 9 is a diagram illustrating an example of how a posture of a user is estimated based on a foot pressure and a motion size according to at least one example embodiment;

DETAILED DESCRIPTION

Figure 1:
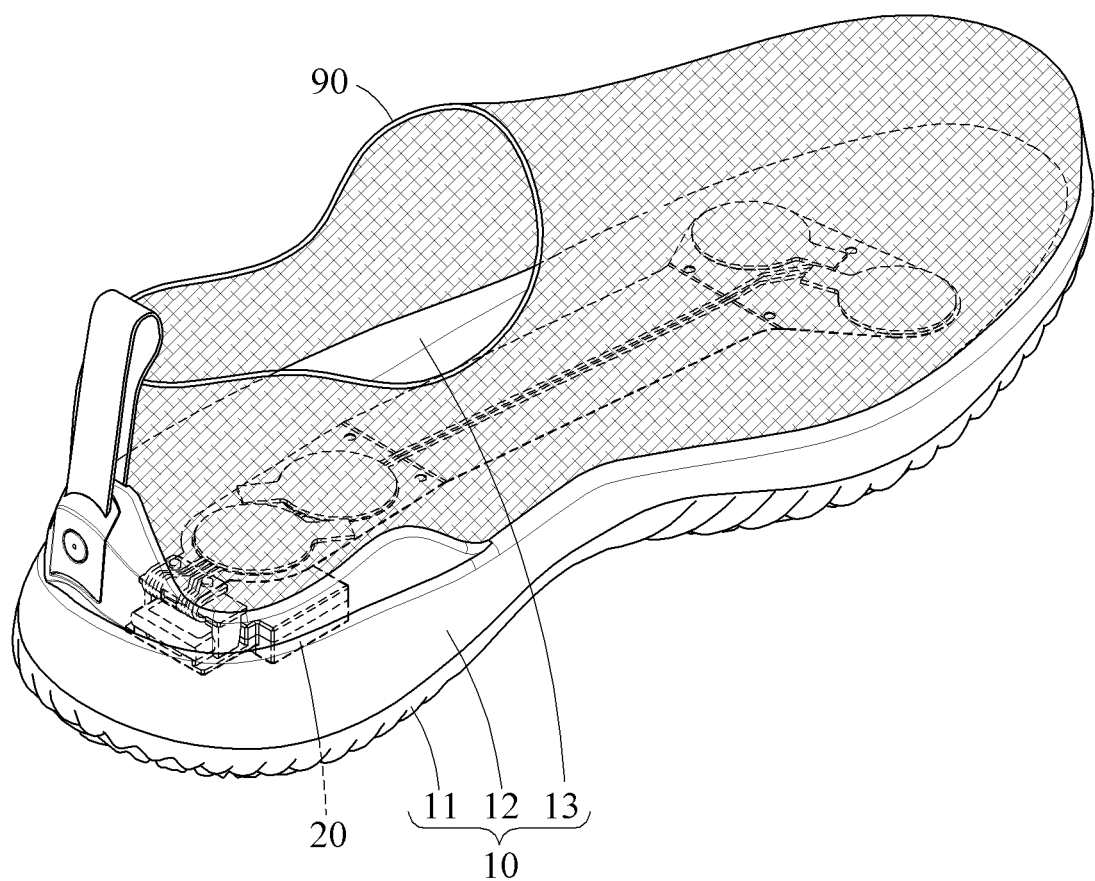
FIG. 1 is a perspective view of a shoe-type device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

A shoe-type device described herein may be referred to as a smart shoe and may include processing circuitry and an electronic element configured to generate vibration. For example, the shoe-type device may include an actuator configured to induce vibration noise by generating physical vibration based on a control signal generated by the processing circuitry. In this example, the actuator may be, for example, a vibrator such as an eccentric motor. The actuator may be embedded in the shoe-type device, and provide a stimulus value less than or equal to a stimulus threshold to a user wearing the shoe-type device. The stimulus threshold may be a minimum value of stimulation applied to activate cells. The actuator may generate stochastic resonance by generating vibration noise having an intensity less than or equal to a tactile sense threshold of a plantar sole of a foot of the user. The stochastic resonance indicates a phenomenon in which, for example, when a measuring device or a sensory organ having a set threshold value receives white noise with less than or equal to the threshold value, a measurement sensitivity to an observation target signal to be observed is improved. For example, the vibration noise generated by the actuator of the shoe-type device may amplify a tactile signal to be transferred to the plantar sole of the user through the stochastic resonance, and thus the user may more sensitively feel stimulation applied onto the plantar sole of the user. Thus, the shoe-type device may help those who are relatively less sensitive to stimulation to their feet to feel normal levels of sensations.

Hereinafter, examples will be described in detail with reference to the accompanying drawings, and like reference numerals in the drawings refer to like elements throughout.

Figure 2:
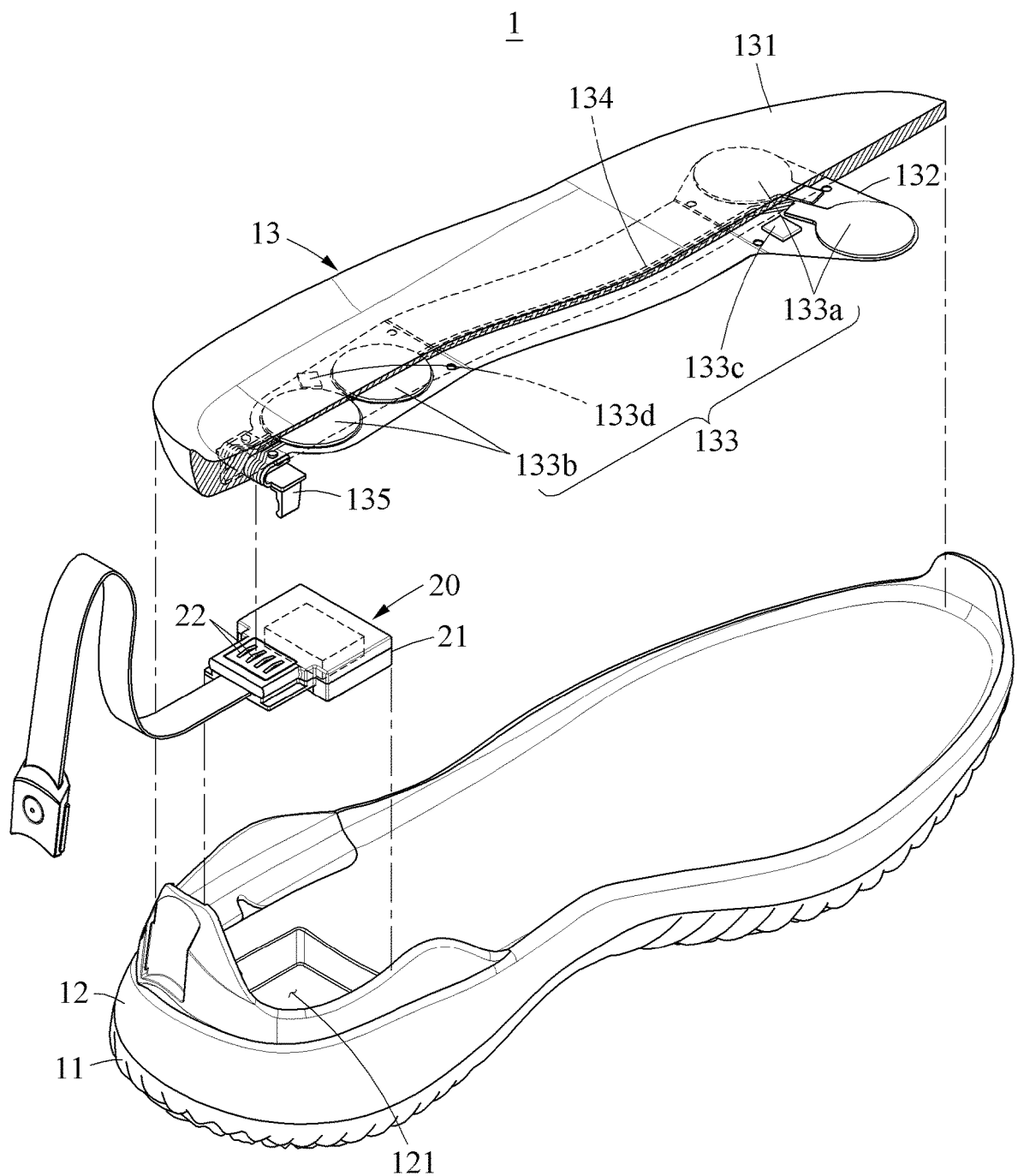
FIG. 2 is an exploded perspective view of a shoe-type device in which an insole body is separated according to at least one example embodiment.
Figure 3:
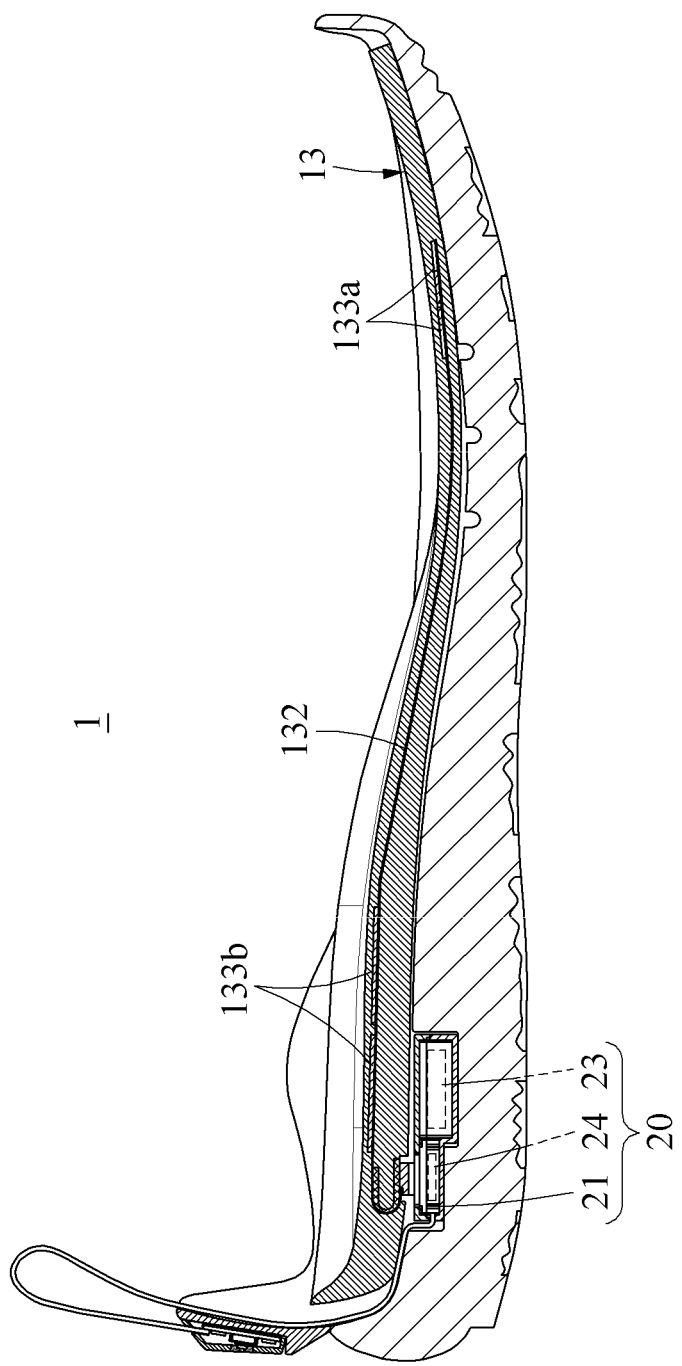
FIG. 3 is a cross-sectional view of a shoe-type device according to at least one example embodiment.

FIG. 1 is a perspective view of a shoe-type device according to at least one example embodiment. FIG. 2 is an exploded perspective view of a shoe-type device in which an insole body is separated according to at least one example embodiment. FIG. 3 is a cross-sectional view of a shoe-type device according to at least one example embodiment.

Referring to FIGS. 1 through 3, a shoe-type device 1 includes a sole 10, a control module 20, and an upper 90. The sole 10 includes an outsole 11, a midsole 12, and an insole 13.

The outsole 11 forms at least a portion of a bottom of the shoe-type device 1. For example, the outsole 11 includes a bottom surface that comes into contact with the ground when a user wears the shoe-type device 1. Hereinafter, the shoe-type device 1 in which the outsole 11 and the midsole 12 are separated from each other will be described. However, the outsole 11 and the midsole 12 may also be provided in an integral form. The midsole 12 forms at least a portion of a lower outer shape. The insole 13 is provided inside the upper 90, and disposed on the midsole 12. The insole 13 includes a surface with which a plantar sole of a foot of the user comes into contact when the user wears the shoe-type device 1, and is detachable from the midsole 12.

The insole 13 includes an insole body 131, a support layer 132, an electronic element 133, a connecting line 134, and a connector 135. The insole body 131 is seated on an upper surface of the midsole 12, and may be provided in various shapes. The support layer 132 is provided on an inner side of the insole body 131 and supports the electronic element 133 and the connecting line 134. The connecting line 134 electrically connects the electronic element 133 and the control module 20, and the connector 135 electrically connects the electronic element 133 to the control module 20.

The electronic element 133 is disposed on an upper surface of the support layer 132, and both the electronic element 133 and the support layer 132 are disposed inside the insole body 131. The electronic element 133 includes an actuator (e.g., an actuator 133a and an actuator 133b as illustrated) and a pressure sensor (e.g., a pressure sensor 133c and a pressure sensor 133d as illustrated). The actuator generates physical vibration having a vibration intensity less than or equal to a set maximum vibration intensity. Herein, the vibration intensity may change irregularly as in a change in noise. The pressure sensor may be a foot pressure sensor, for example, a piezoelectric pressure sensor and a force-sensitive resistor (FSR), which is configured to measure or sense a foot pressure transferred from the plantar sole of the user when the user wears the shoe-type device 1.

According to an example, the electronic element 133 may further include a motion sensor or an inertia sensor. The motion sensor refers to a sensor, for example, an acceleration sensor, which is configured to measure or sense a motion or a movement of the shoe-type device 1 or the user wearing the shoe-type device 1. The motion sensor is disposed at various positions including, for example, in the support layer 132, in the shoe-type device 1. For example, the motion sensor may also be disposed in the control module 20, the sole 10, or the upper 90.

The control module 20 is electrically connected to the electronic element 133, and receives sensor data from the pressure sensor or the motion sensor that is included in the electronic element 133. In addition, the control module 20 transmits, to the actuator, a control signal to control the actuator.

The control module 20 includes a case 21, a connecting portion 22, a battery 23, and a processor 24.

The case 21 is provided in a shape corresponding to a receiving groove 121 formed in the midsole 12. The connecting portion 22 includes a terminal to be electrically connected to the connecting line 134, and is disposed on an upper side of the case 21. The battery 23 supplies power to the electronic element 133 and the processor 24.

In addition to the processor 24, the control module 10 may also include a memory containing instructions that, when executed by the processor 24, configure the processor 24 as a special purpose processor to generate a control signal to control an operation of the electronic element 133. For example, when the electronic element 133 includes a vibrator, the processor 24 may generate a control signal to amplify a level of a signal associated with a stimulation that is too low for a user to sense by adding white noise, which has a wide frequency range, to the signal to cause a portion of the white noise having the same frequency as the signal to resonate with the signal thus amplifying the signal and allowing the user to sense the stimulation.

For example, the processor 24 may generate a control signal to control activation of the actuator and/or adjust a frequency (or the number of vibrations) or the maximum vibration intensity of the actuator, based on the sensor data. More specifically, the processor 24 may be configured as a special purpose processor determine whether a user is sitting, standing or walking, and deactivate the actuator when the user is sitting and/or automatically adjust a maximum vibration intensity of the actuator based on a foot pressure when the user is standing or waking. Therefore, the processor 24 may improve the functioning of the smart shoe 1 itself by reducing power consumption of the battery 23 and/or increasing comfortableness that may be experienced by the user.

Figure 4:
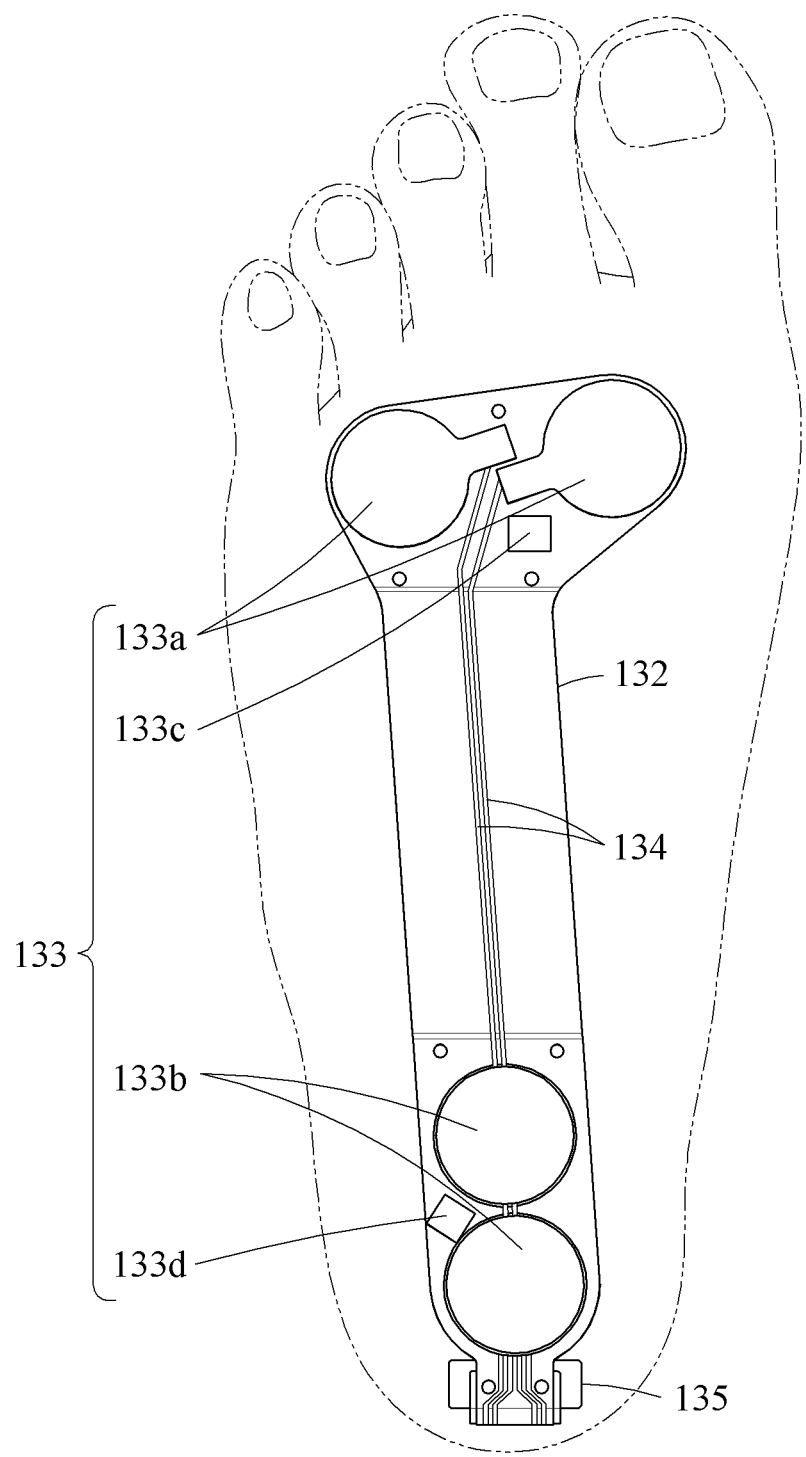
FIG. 4 is a top view illustrating a relative positional relationship between an electronic element and a foot of a user according to at least one example embodiment.

FIG. 4 is a top view illustrating a relative positional relationship between an electronic element and a foot of a user according to at least one example embodiment.

Referring to FIG. 4, the electronic element 133 includes a front actuator 133a disposed at a front side of the support layer 132, a rear actuator 133b disposed at a rear side of the support layer 132, a front pressure sensor 133c disposed in an area adjacent to an area in which the front actuator 133a is disposed, and a rear pressure sensor 133d disposed in an area adjacent to an area in which the rear actuator 133b is disposed. The front actuator 133a generates vibration noise in a front portion of a foot of a user wearing the shoe-type device 1, and the rear actuator 133b generates vibration noise in a rear portion of the foot of the user. In an example, the processor 24 is configured to determine a maximum vibration intensity of the front actuator 133a based on a foot pressure measured by the front pressure sensor 133c, and determine a maximum vibration intensity of the rear actuator 133b based on a foot pressure measured by the rear pressure sensor 133d.

The shoe-type device 1 receives power from the battery 23 embedded in the shoe-type device 1 for portability as described above, and it may thus be important to reduce (or, alternatively, minimize) a power consumption of the battery 23 and increase an available amount of time to use the shoe-type device 1. As such, permanently activating or operating the actuators 133a and 133b included in the shoe-type device 1 may consume a great amount of power, and thus result in degradation of usability of the shoe-type device 1. Therefore, in one or more example embodiments, the processor 24 may smartly control the activation or operation of the actuators 133a and 133b based on a situation to reduce the power consumption of the battery 23.

Figure 5:
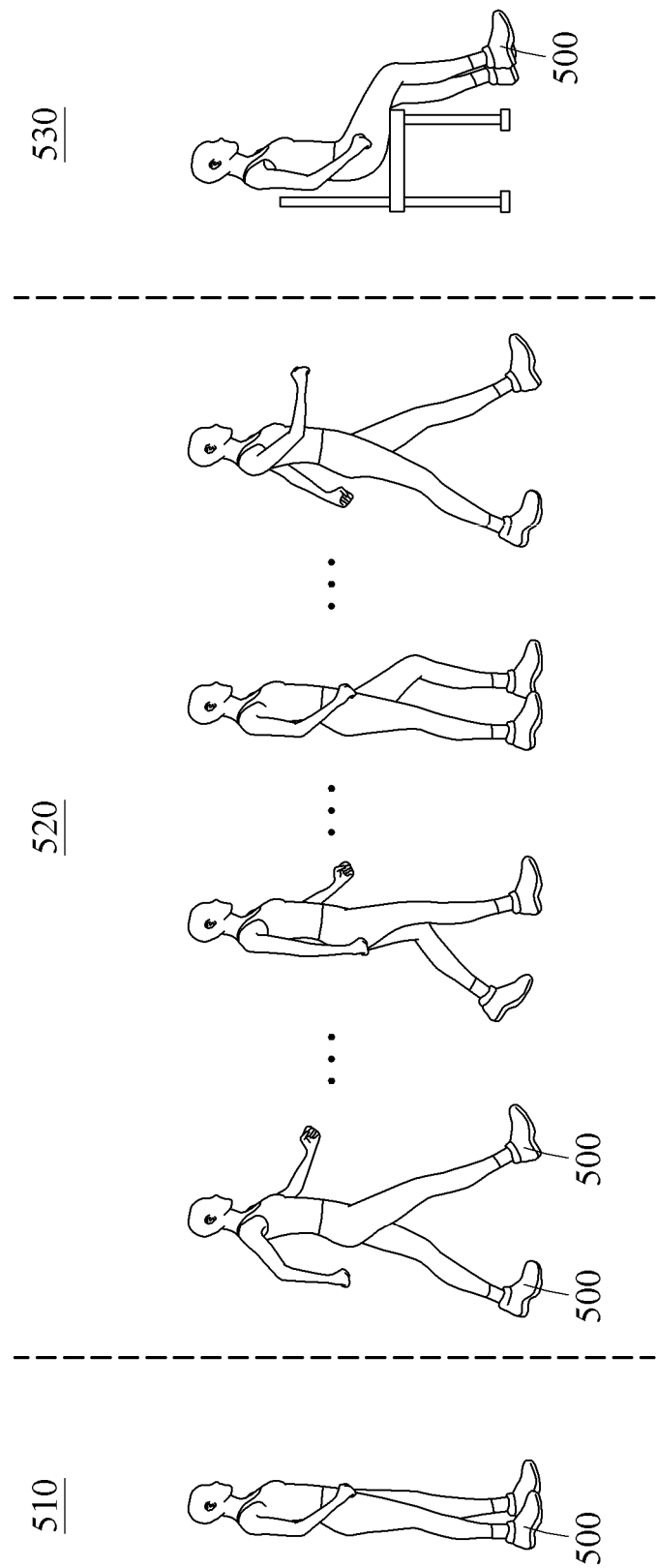
FIG. 5 is a diagram illustrating examples of various postures of a user wearing a shoe-type device according to at least one example embodiment.

FIG. 5 is a diagram illustrating examples of various postures of a user wearing a shoe-type device according to at least one example embodiment.

Referring to FIG. 5, a shoe-type device 500 determines whether a posture of a user wearing the shoe-type device 500 is a standing posture 510, a walking posture 520, or a sitting posture 530.

It may be desirable for the shoe-type device 500 to generate vibration noise to induce stochastic resonance when the user is standing or walking, but such vibration may not be needed when the user is sitting. This is because the need to feel a sensation on a plantar sole of a foot of the user when the user is sitting may be less than the need to feel a sensation on the plantar sole when the user is standing or walking. Thus, when the user is sitting, vibration generated by the shoe-type device 500 may make the user rather uncomfortable.

According to at least one example embodiment to be described hereinafter, a shoe-type device may determine whether to operate an actuator in a current situation based on sensor data. When the shoe-type device determines that there is no need to operate the actuator, the shoe-type device may stop operating the actuator or deactivate the actuator to reduce a power consumption of a battery thereof, and thus increase an available amount of time to use the shoe-type device. In addition, by stopping operation of the actuator, the shoe-type device may reduce inconvenience or uncomfortableness that may be felt by a user wearing the shoe-type device.

Figure 6:
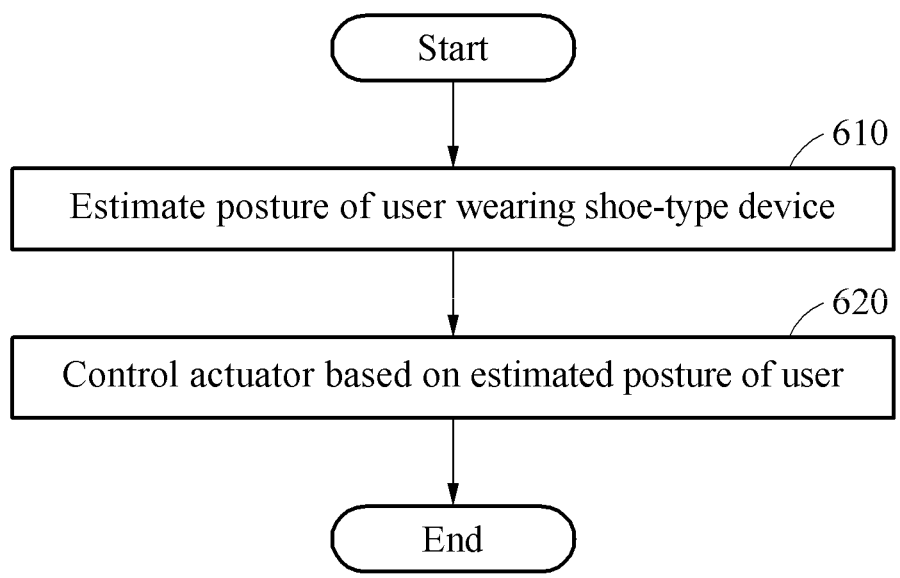
FIGS. 6 and 7 are flowcharts illustrating an example of a control method of a shoe-type device according to at least one example embodiment.
Figure 7:
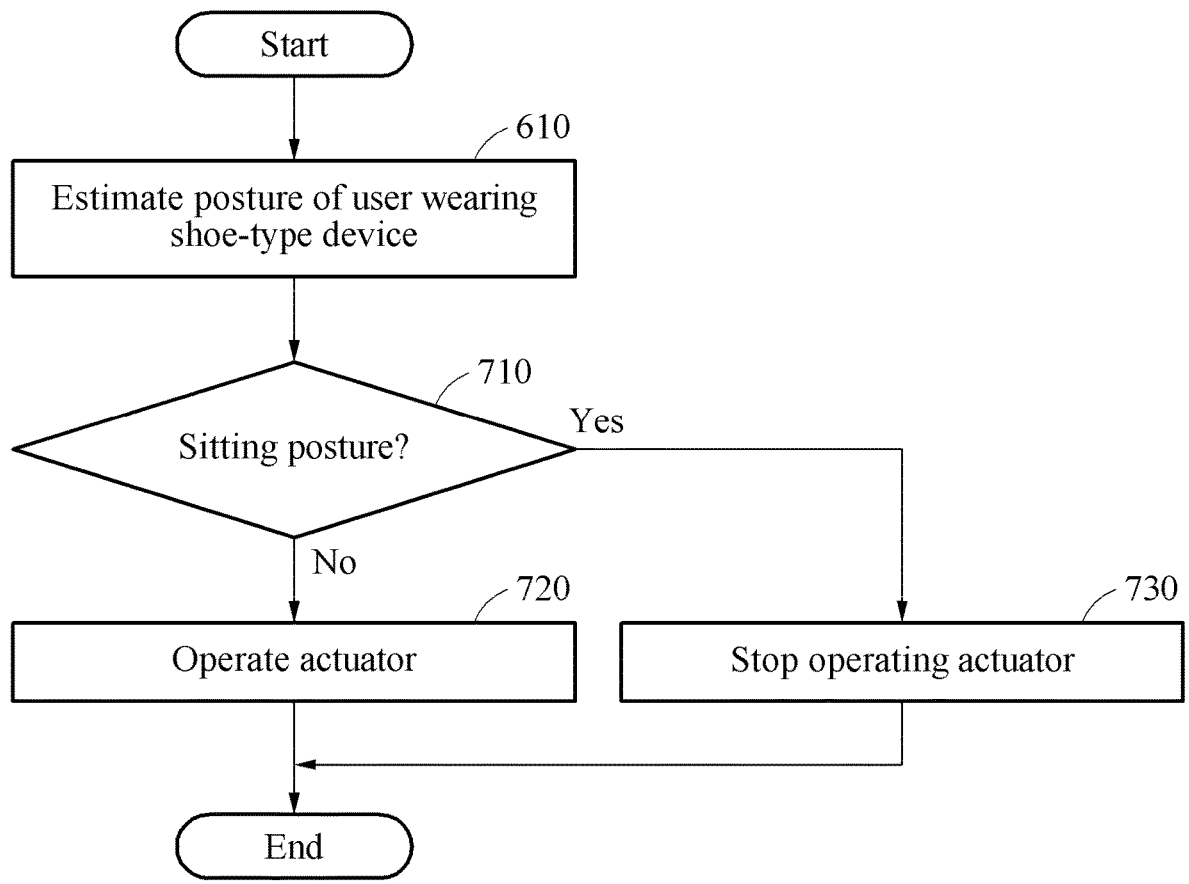

FIGS. 6 and 7 are flowcharts illustrating an example of a control method of a shoe-type device according to at least one example embodiment.

Referring to FIG. 6, in operation 610, the processor 24 of the shoe-type device 1 may estimate a posture of a user wearing the shoe-type device. To estimate the posture of the user, the processor 24 may use sensor data output from at least one sensor included in the electronic element 133. For example, the processor 24 may determine whether the user is currently standing or walking, or sitting based on sensor data obtained from a foot pressure sensor and/or a motion sensor included in the electronic element 133.

In an example, the shoe-type device may estimate a posture of the user based on a foot pressure measured by the foot pressure sensor and a change in foot pressure over time. For example, when the foot pressure is greater than a first threshold value, and there is no or insignificant change in foot pressure over time or the change in foot pressure over time is in a certain range, the posture of the user may be estimated to be a standing posture. When the foot pressure is less than a second threshold value, and there is no or insignificant change in foot pressure over time or the change in foot pressure over time is in the range, the posture of the user may be estimated to be a sitting posture. When the foot pressure changes in a certain pattern with time, the posture of the user may be estimated to be a walking posture. In this example, the first threshold value may be the same as the second threshold value, or greater than the second threshold value.

In another example, the shoe-type device may include both the foot pressure sensor and the motion sensor, and the processor 24 may estimate a posture of the user based on foot pressure information obtained from the foot pressure sensor and motion information obtained from the motion sensor. In this example, a motion of the user may be measured through the motion sensor such as an acceleration sensor. When a spatial size of an acceleration value measured by the acceleration sensor exceeds a certain value, the shoe-type device may estimate that the user is currently moving. When both a foot pressure measured by the foot pressure sensor and a motion size measured by the motion sensor are small, the shoe-type device may estimate that the user is currently sitting. For example, when the measured foot pressure is less than or equal to a first threshold value and the measured motion size is less than or equal to a second threshold value, the shoe-type device may determine the posture of the user to be the sitting posture. However, in other situations or cases, the shoe-type device may determine the posture of the user not to be the sitting posture.

In operation 620, the processor 24 of the shoe-type device 1 may control the actuator included in the electronic element 133 based on the posture of the user estimated in operation 610. The shoe-type device may determine whether to operate the actuator or stop operating the actuator based on the posture of the user. When it is determined to stop operating the actuator, the shoe-type device determines a maximum vibration intensity of the actuator based on a foot pressure measured by the foot pressure sensor. Hereinafter, operation 620 will be described in further detail with reference to FIG. 7.

Referring to FIG. 7, in operation 710, the processor 24 of the shoe-type device 1 determines whether a current posture of the user is a sitting posture or not based on sensor data. In operation 720, when the posture of the user is estimated not to be the sitting posture, the processor 24 of the shoe-type device 1 operates the actuator. Herein, for example, when the actuator continues operating from a previous time, the shoe-type device may continue to operate the actuator.

In addition, when operating the actuator, the processor 24 of the shoe-type device 1 may control a vibration output of the actuator. In an example, the processor 24 of the shoe-type device 1 may determine a maximum vibration intensity of the actuator based on sensor data of the foot pressure sensor configured to sense a foot pressure of the user. For example, when the foot pressure increases within a certain range, the processor 24 of the shoe-type device 1 may set the maximum vibration intensity of the actuator to be greater. For example, the processor 24 of the shoe-type device 1 may set a first maximum vibration intensity of the actuator corresponding to a first foot pressure and a second maximum vibration intensity of the actuator corresponding to a second foot pressure to be different from each other. In this example, the first foot pressure and the second foot pressure may be different from each other. An intensity of the vibration output generated by the actuator may change within the set maximum vibration intensity. As described, the processor 24 of the shoe-type device 1 may adjust a maximum vibration intensity of the actuator based on a measured foot pressure to reduce a power consumption of the battery 23 thereof and reduce inconvenience or uncomfortableness that may be felt by the user.

In operation 730, when the posture of the user is estimated to be the sitting posture, the processor 24 of the shoe-type device 1 deactivates the actuator or stops operating the actuator, or sets the actuator to be in a standby state.

As described above, the processor 24 of the shoe-type device 1 may determine whether there is a need to activate or operate the actuator, for example, when the user is standing or walking. When there is no need to activate or operate the actuator, the processor 24 of the shoe-type device 1 may deactivate the actuator or stop operating the actuator, or set the actuator to be in a standby state, and may thus reduce a power consumption of the battery 23 and increase an available amount of time to use the shoe-type device 1.

Figure 8A:
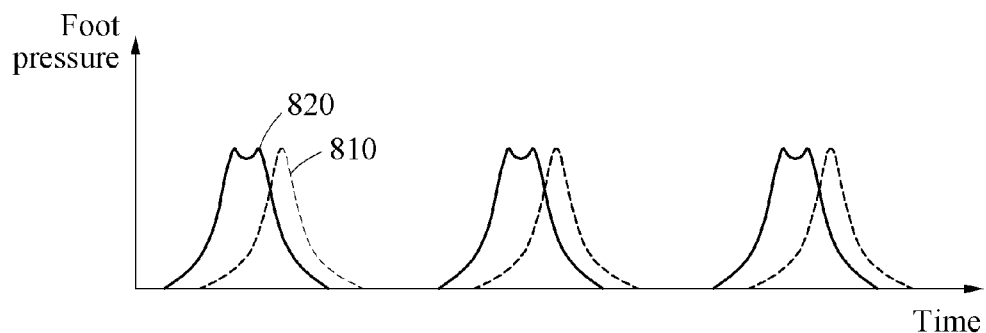
FIGS. 8A through 8C are diagrams illustrating an example of how a posture of a user is estimated based on a foot pressure according to at least one example embodiment.
Figure 8B:
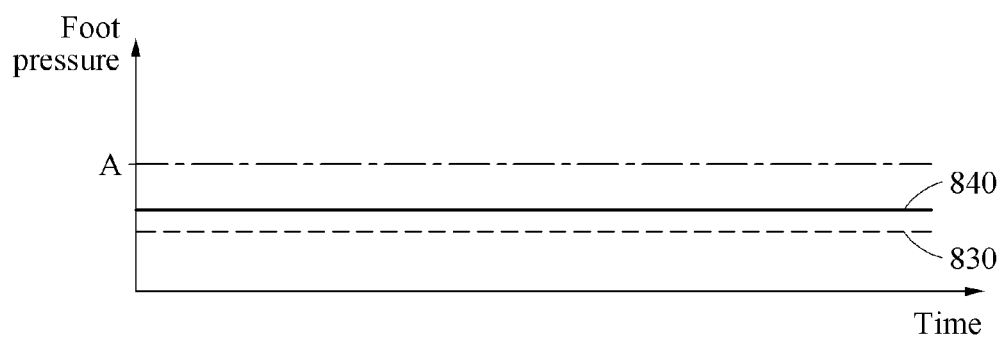
Figure 8C:
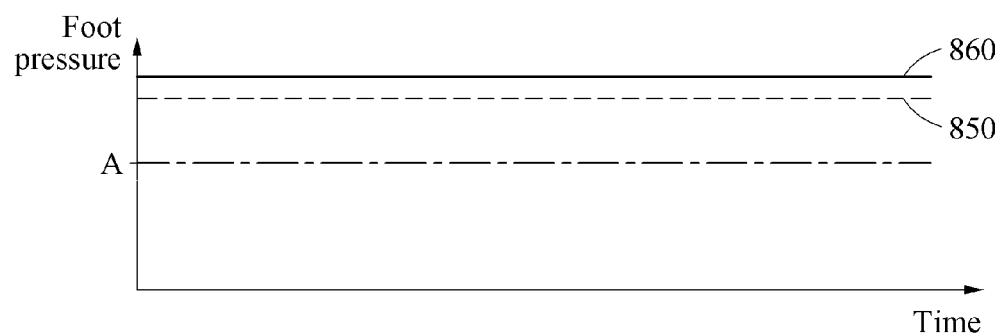

FIGS. 8A through 8C are diagrams illustrating an example of how a posture of a user is estimated based on a foot pressure according to at least one example embodiment.

FIGS. 8A, 8B, and 8C illustrate changes in foot pressure based on a time at which a foot pressure is measured from each of different postures of a user wearing a shoe-type device. FIG. 8A illustrates a change 810 of a foot pressure measured when the user is walking by a first foot pressure sensor disposed at a front side of a plantar sole of a foot of the user, and a change 820 of a foot pressure measured when the user is walking by a second foot pressure sensor disposed at a rear side of the plantar sole of the foot of the user. In such a situation where the user is walking, the foot pressure may relatively drastically change over time, and a certain pattern may be repetitively shown. Thus, when a change in foot pressure over time is relatively large, and the change in foot pressure repeats by a certain pattern, the processor 24 of the shoe-type device 1 may estimate a current posture of the user as a walking posture.

FIG. 8B illustrates a change 830 of a foot pressure measured by the first pressure sensor and a change 840 of a foot pressure measured by the second foot pressure sensor, when the user is sitting. In such a situation where the user is sitting, the foot pressure may be relatively small, and a change in foot pressure over time may also be relatively small. Thus, when a foot pressure is less than a threshold value, for example, A as illustrated in FIG. 8B, and a change in foot pressure over time is relatively small, the processor 24 of the shoe-type device 1 may estimate a current posture of the user as a sitting posture.

FIG. 8C illustrates a change 850 of a foot pressure measured by the first pressure sensor and a change 860 of a foot pressure measured by the second foot pressure sensor, when the user is standing. In such a situation where the user is standing, the foot pressure may be relatively large, and a change in foot pressure over time may be relatively small. Thus, when a foot pressure is greater than a threshold value, for example, A as illustrated in FIG. 8C, and a change in foot pressure over time is relatively small, the processor 24 of the shoe-type device 1 may estimate a current posture of the user as a standing posture.

FIG. 9 is a diagram illustrating an example of how a posture of a user is estimated based on a foot pressure and a motion size according to at least one example embodiment.

Referring to FIG. 9, the processor 24 of the shoe-type device 1 may classify a current posture of a user wearing the shoe-type device into four postures based on a foot pressure and a motion size. The processor 24 of the shoe-type device 1 may control an actuator based on the current posture of the user.

For example, when both a foot pressure and a motion size are relatively large, the processor 24 of the shoe-type device 1 may determine a posture of the user to be a heel-landing posture. When a foot pressure is relatively small although a motion size is relatively large, the processor 24 of the shoe-type device 1 may determine a posture of the user to be a toe-off or swing posture. When a foot pressure is relatively large although a motion size is relatively small, the processor 24 of the shoe-type device 1 may determine a posture of the user to be a standing posture. When both a foot pressure and a motion size are relatively small, the processor 24 of the shoe-type device 1 may determine a posture of the user to be a sitting posture. In this example, the heel-landing posture, and the toe-off or swing posture may be included in a walking posture.

When the posture of the user is determined to be the standing posture or the walking posture, the shoe-type device may determine to activate or operate the actuator. When the posture of the user is determined to be the sitting posture, the shoe-type device may determine to deactivate the actuator or stop operating the actuator.

A range 910 indicated by hatched lines in FIG. 9 may indicate a range needed to distinguish postures of the user based on a boundary value. For example, when a foot pressure and a motion size are in the range 910, the processor 24 of the shoe-type device 1 may control the actuator to maintain its previous state. In this example, when the actuator is previously operating, the processor 24 of the shoe-type device 1 may continue to operate the actuator. When the actuator is previously deactivated, the processor 24 of the shoe-type device 1 may maintain the actuator in a deactivated state.

Figure 10:
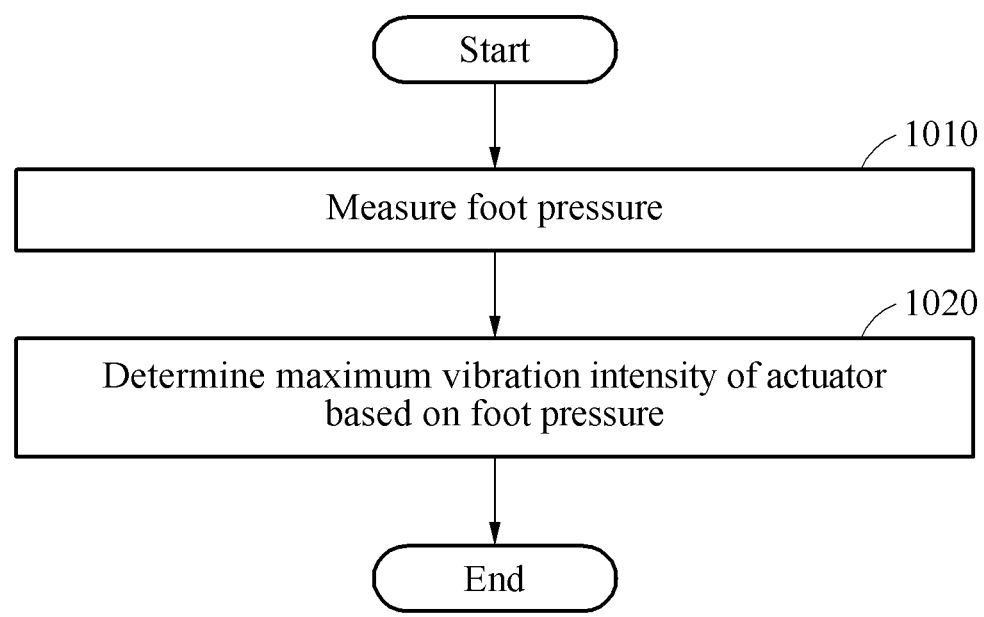
FIG. 10 is a flowchart illustrating another example of a control method of a shoe-type device according to at least one example embodiment.

FIG. 10 is a flowchart illustrating another example of a control method of a shoe-type device according to at least one example embodiment.

Referring to FIG. 10, in operation 1010, the processor 24 of the shoe-type device 1 may measure a foot pressure through a foot pressure sensor. In operation 1020, the processor 24 of the shoe-type device 1 may determine a maximum vibration intensity of an actuator based on the measured foot pressure. In an example, the processor 24 of the shoe-type device 1 may set a first maximum vibration intensity of the actuator corresponding to a first foot pressure and a second maximum vibration intensity of the actuator corresponding to a second foot pressure to be different from each other. In this example, the processor 24 of the shoe-type device 1 may set the maximum vibration intensity of the actuator to be small when the foot pressure is small, and set the maximum vibration intensity of the actuator to be great when the foot pressure is great. Thus, a foot pressure and a maximum vibration intensity to be set based on the foot pressure may be in a linear or nonlinear relationship.

In an example, the shoe-type device may include a first actuator disposed in a first area, for example, a front portion, of the shoe-type device, and a second actuator disposed in a second area, for example, a rear portion, of the shoe-type device. In this example, a first foot pressure sensor may be disposed in an area adjacent to the first area, and a second foot pressure sensor may be disposed in an area adjacent to the second area. In this example, the processor 24 of the shoe-type device 1 may determine a maximum vibration intensity of the first actuator based on a foot pressure measured by the first foot pressure sensor, and determine a maximum vibration intensity of the second actuator based on a foot pressure measured by the second foot pressure sensor. Thus, in detailed steps of walking including, for example, a toe-off posture and a heel-landing posture, it is possible to individually control the actuators.

A maximum vibration intensity may be set to be less than or equal to a threshold value, although an intensity of vibration generated by the actuator changes frequently. The set maximum vibration intensity may not be suitable for some environments or conditions. Thus, when an intensity of vibration of the actuator to be applied to the user wearing the shoe-type device exceeds the threshold value based on a foot pressure, the user may experience inconvenience or uncomfortableness by such excessive vibration, and noise and unnecessary power consumption of a battery may occur. For example, when the user takes a foot of the user off the ground, a space between a plantar sole of the foot of the user and an insole of the shoe-type device may increase. In this example, when an intensity of vibration of the actuator increases to be greater than need be, the user may feel uncomfortable thereby. Therefore, in one or more example embodiments, the processor 24 of the shoe-type device 1 may automatically adjust a maximum vibration intensity of the actuator based on a foot pressure as described herein, to reduce an unnecessary power consumption of the battery 23 and the uncomfortableness that may be experienced by the user.

Figure 11A:
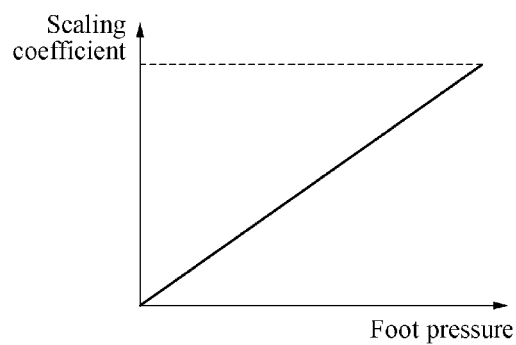
FIGS. 11A through 11C are diagrams illustrating an example of how a maximum vibration intensity of an actuator is adjusted based on a foot pressure according to at least one example embodiment.
Figure 11B:
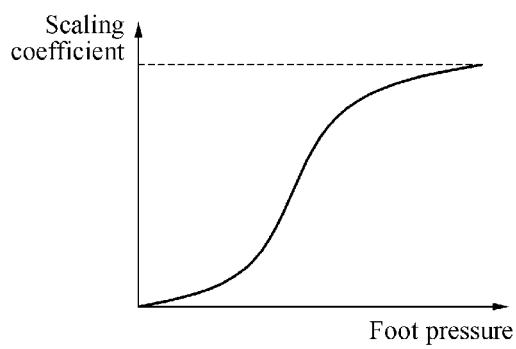
Figure 11C:
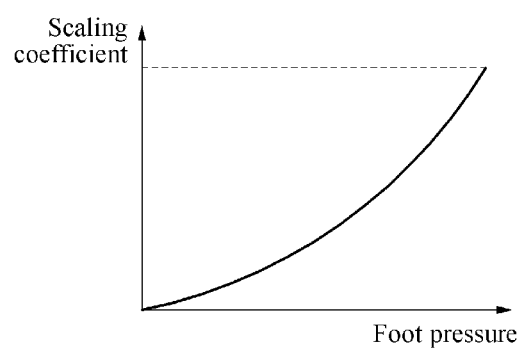

FIGS. 11A through 11C are diagrams illustrating an example of how a maximum vibration intensity of an actuator is adjusted based on a foot pressure according to at least one example embodiment.

FIG. 11A illustrates an example of a linear change of a scaling coefficient to be applied to a maximum vibration intensity of an actuator based on a foot pressure. FIGS. 11B and 11C illustrate examples of a nonlinear change of a scaling coefficient to be applied to a maximum vibration intensity of the actuator based on a foot pressure. In these examples, a maximum vibration intensity of the actuator may change based on a scaling coefficient to be applied thereto. The processor 24 of the shoe-type device 1 may set the maximum vibration intensity to be small when the foot pressure is small, and set the maximum vibration intensity to be great when the foot pressure is great. Thus, by controlling the actuator accordingly as described above, the processor 24 of the shoe-type device 1 may reduce inconvenience or uncomfortableness that may be experienced by a user wearing the shoe-type device due to an excessive intensity of vibration.

Figure 12:
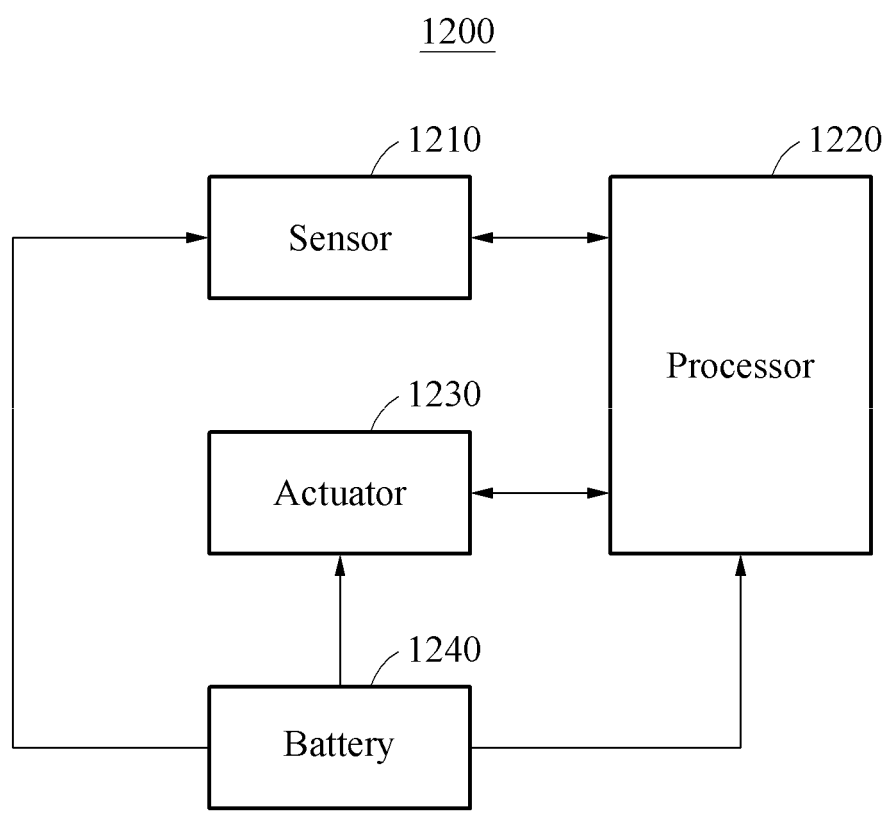
FIG. 12 is a diagram illustrating an example of a control device of a shoe-type device according to at least one example embodiment.

FIG. 12 is a diagram illustrating an example of a control device of a shoe-type device according to at least one example embodiment.

Referring to FIG. 12, a control device 1200 of a shoe-type device includes a sensor 1210, a processor 1220, an actuator 1230, and a battery 1240. The control device 1200 may be embedded in the shoe-type device and operate therein.

The sensor 1210 may include a foot pressure sensor configured to measure a foot pressure of a user wearing the shoe-type device, and/or a motion sensor configured to measure a motion of the user wearing the shoe-type device. The foot pressure sensor may be disposed in a sole of the shoe-type device, and the motion sensor may be disposed in the sole and/or an upper of the shoe-type device.

The battery 1240 provides power to each component of the shoe-type device.

The processor 1220 controls each component of the shoe-type device. The processor 1220 estimates a posture of the user wearing the shoe-type device based on sensor data obtained from the sensor 1210, and determines whether to operate the actuator 1230 based on the estimated posture of the user. For example, when the posture of the user is estimated to be a sitting posture, the processor 1220 may generate a control signal to stop operating the actuator 1230 or set the actuator 1230 to be in a standby state. For another example, when the posture of the user is not estimated to be the sitting posture, the processor 1220 may determine to operate the actuator 1230.

In this example, when the processor 1220 determines to operate the actuator 1230, the processor 1220 may determine a maximum vibration intensity of the actuator 1230 based on a foot pressure of a foot of the user. For example, the processor 1220 may determine a first maximum vibration intensity of the actuator corresponding to a first foot pressure and a second maximum vibration intensity of the actuator corresponding to a second foot pressure to be different from each other. In this example, the processor 1220 may set the maximum vibration intensity of the actuator to be greater when the foot pressure increases within a range.

The actuator 1230 generates vibration to apply nerve stimulation to the foot of the user based on a control signal generated by the processor 1220. In an example, the actuator 1230 may include a first actuator disposed in a first area of the shoe-type device, and a second actuator disposed in a second area of the shoe-type device. In this example, the foot pressure sensor may include a first foot pressure sensor disposed in an area adjacent to the first area, and a second foot pressure sensor disposed in an area adjacent to the second area. In this example, the processor 1220 may determine a maximum vibration intensity of the first actuator based on a foot pressure measured by the first foot pressure sensor, and a maximum vibration intensity of the second actuator based on a foot pressure measured by the second foot pressure sensor.

The processor 1220 may also perform at least one of control operations for the shoe-type device described above, and a repeated and detailed description thereof is omitted here for increased clarity and conciseness.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of controlling a smart shoe, the smart shoe including an actuator and at least one sensor, the method comprising:
    estimating, via processing circuitry, whether a posture of a user wearing the smart shoe is a walking posture, a standing posture or a sitting posture based on sensor data output from the sensor to generate an estimated posture; and
    controlling, via the processing circuitry, the actuator by continuously outputting a power to the actuator to provide a stochastic resonance to a user in response to the estimated posture of the user being one or more of the walking posture or the standing posture, and cutting off the power to the actuator in response to the estimated posture of the user being the sitting posture.

2. The method of claim 1, wherein the sensor includes a foot pressure sensor configured to measure a foot pressure of the user to generate the sensor data, and the controlling comprises:
    determining a maximum vibration intensity of the actuator based on the sensor data.

3. The method of claim 2, wherein the determining the maximum vibration intensity of the actuator comprises:
    increasing the maximum vibration intensity in response to the foot pressure increasing within a range.

4. The method of claim 2, wherein the determining the maximum vibration intensity of the actuator comprises:
    setting a first maximum vibration intensity of the actuator based on a first foot pressure associated with a first foot of the user, and
    setting a second maximum vibration intensity of the actuator based on a second foot pressure associated with a second foot of the user such that the second maximum vibration intensity is different from the first maximum vibration intensity.

5. The method of claim 1, wherein the sensor includes a foot pressure sensor, and wherein the estimating the posture comprises:
    estimating the posture of the user based on a foot pressure measured by the foot pressure sensor and a change in foot pressure over time to generate the estimated posture.

6. The method of claim 1, wherein the sensor includes a foot pressure sensor and a motion sensor, the foot pressure sensor configured to measure foot pressure to generate foot pressure information and the motion sensor configured to measure motion size to generate motion information, and wherein the estimating the posture comprises:
    estimating the posture of the user based on the foot pressure information and the motion information to generate the estimated posture.

7. The method of claim 6, wherein the estimating of the posture comprises:
    determining the estimated posture of the user as the sitting posture, in response to the foot pressure being less than or equal to a first threshold value and the motion size being less than or equal to a second threshold value.

8. A non-transitory computer-readable medium comprising computer readable instructions that, when executed, cause a computer to perform the method of claim 1.

9. A smart shoe comprising:

an actuator;

a foot pressure sensor configured to measure a foot pressure to generate foot pressure information; and a processor configured to, estimate whether a posture of a user wearing the smart shoe is a walking posture, a standing posture or a sitting posture based on at least the foot pressure information to generate an estimated posture, and control the actuator by continuously outputting a power to the actuator to provide a stochastic resonance to a user in response to the estimated posture of the user being one or more of the walking posture or the standing posture, and cutting off the power to the actuator in response to the estimated posture of the user being the sitting posture.

10. The smart shoe of claim 9, wherein the processor is further configured to determine a maximum vibration intensity of the actuator based on the foot pressure measured by the foot pressure sensor.

11. The smart shoe of claim 9, further comprising:

a motion sensor configured to measure a motion of the smart shoe to generate motion information, wherein the processor is configured to control the actuator based on the foot pressure information and the motion information.

12. The smart shoe of claim 11, wherein the foot pressure sensor is in a sole of the smart shoe, and the motion sensor is in at least one of the sole or an upper of the smart shoe.

13. The smart shoe of claim 9, wherein the actuator is configured to provide the stochastic resonance via nerve stimulation to a foot of the user.

14. A smart shoe comprising:

an actuator;

a foot pressure sensor configured to measure a foot pressure of a user wearing the smart shoe to generate foot pressure information; and a processor configured to, estimate whether a posture of the user wearing the smart shoe is a walking posture, a standing posture or a sitting posture based on at least the foot pressure information to generate an estimated posture, control the actuator by continuously outputting a power to the actuator to provide a stochastic resonance to a user in response to the estimated posture of the user being one or more of the walking posture or the standing posture, set a maximum vibration intensity of the actuator based on at least the foot pressure information, and cut off the power to the actuator in response to the estimated posture of the user being the sitting posture.

15. The smart shoe of claim 14, wherein the processor is further configured to increasing the maximum vibration intensity in response to the foot pressure increasing within a range.

16. The smart shoe of claim 14, wherein the processor is configured to control the maximum vibration intensity by, setting a first maximum vibration intensity of the actuator based on a first foot pressure associated with a first foot of the user, and setting a second maximum vibration intensity of the actuator based on a second foot pressure associated with a second foot of the user such that the second maximum vibration intensity is different from the first maximum vibration intensity.

17. The smart shoe of claim 14, wherein the actuator includes a first actuator and a second actuator, the first actuator being in a first area of the smart shoe and the second actuator being in a second area of the smart shoe, and the foot pressure sensor includes a first foot pressure sensor and a second foot pressure sensor, the first foot pressure sensor being in an area adjacent to the first area and the second foot pressure sensor being in an area adjacent to the second area.

18. The smart shoe of claim 17, wherein the processor is further configured to, determine a maximum vibration intensity of the first actuator based on the foot pressure measured by the first foot pressure sensor; and determine a maximum vibration intensity of the second actuator based on the foot pressure measured by the second foot pressure sensor.

* * * * *